(12) United States Patent
Wood et al.

(10) Patent No.: US 8,434,486 B2
(45) Date of Patent: May 7, 2013

(54) SUPRAGLOTTIC FIXATION DEVICE FOR ENDOTRACHEAL TUBES

(75) Inventors: Lockett E. Wood, Lyons, CO (US); Nicole McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 613 days.

(21) Appl. No.: 12/642,565

(22) Filed: Dec. 18, 2009

(65) Prior Publication Data
US 2011/0146690 A1 Jun. 23, 2011

(51) Int. Cl.
*A61M 16/00* (2006.01)

(52) U.S. Cl.
USPC .................................................. 128/207.14

(58) Field of Classification Search .............. 128/207.14, 128/207.15, 207.16, 207.18; 604/96.01, 604/101.01, 101.05, 102.01–102.03, 915, 604/916, 104–106; 606/191–194
See application file for complete search history.

(56) References Cited

U.S. PATENT DOCUMENTS

| | | | |
|---|---|---|---|
| 4,091,816 A * | 5/1978 | Elam | 128/207.15 |
| 4,141,364 A | 2/1979 | Schultze | |
| 4,231,365 A | 11/1980 | Scarberry | |
| 4,235,239 A | 11/1980 | Elam | |
| 4,341,210 A | 7/1982 | Elam | |
| 4,423,725 A | 1/1984 | Baran et al. | |
| 4,573,966 A * | 3/1986 | Weikl et al. | 604/509 |
| 4,976,261 A | 12/1990 | Gluck et al. | |
| 5,033,466 A | 7/1991 | Weymuller, Jr. | |
| 5,315,992 A | 5/1994 | Dalton | |
| 6,070,581 A | 6/2000 | Augustine et al. | |
| 6,164,277 A | 12/2000 | Meredith | |
| 6,500,146 B1 * | 12/2002 | Pinchuk et al. | 604/96.01 |
| 6,729,325 B2 | 5/2004 | Alfery | |
| 6,802,317 B2 | 10/2004 | Gobel | |
| 6,840,242 B1 | 1/2005 | McCoy | |
| 7,174,889 B2 | 2/2007 | Boedeker et al. | |
| 7,331,346 B2 | 2/2008 | Zocca et al. | |
| 7,777,399 B2 * | 8/2010 | Eidenschink et al. | 604/96.01 |
| 2004/0116898 A1 | 6/2004 | Hawk | |
| 2007/0137652 A1 | 6/2007 | Qureshi et al. | |
| 2008/0041392 A1 | 2/2008 | Cook | |
| 2008/0078398 A1 | 4/2008 | Cook | |
| 2008/0078402 A1 | 4/2008 | Mongeon | |
| 2008/0257356 A1 | 10/2008 | Swick | |
| 2008/0276936 A1 | 11/2008 | Cook | |
| 2009/0101140 A1 | 4/2009 | Miller et al. | |

OTHER PUBLICATIONS

Dullenkopf; Air Leakage Around Endotracheal Tube Cuffs; European Journal of Anaesthiology 2004, pp. 448-453, vol. 21.
Sinha et al.; Supraglottic Airway Devices Other Than Laryngeal Mask Airway and its Prototypes; Indian J. Anaesth. 2005; 49 (4) : 281-292.
Park et al.,; The Influence of Head and Neck Position on the Oropharyngeal Leak Pressure and Cuff Position of Three Supraglottic Airway Devices; 2009; pp. 112-117; vol. 108(1).
Microcuff Endotracheal Tube and Pediatric ETT; http://www.kchealthcare.com/productpromosite/microcuff/www/Index.asp?action=Main; last viewed Mar. 31, 2010.

* cited by examiner

*Primary Examiner* — Manuel Mendez

(57) ABSTRACT

According to various embodiments, an endotracheal tube ventilating device with a sealing cuff includes an anchoring device. The anchoring device may be secured to the tube above the sealing cuff and extend outwardly from the tubular body. In addition, the anchoring device may be configured to be positioned completely within the hypopharynx of a patient, in contact with the piriform fossa and a laryngeal surface of the epiglottis without creating an airtight seal of the hypopharynx or the esophagus.

21 Claims, 4 Drawing Sheets

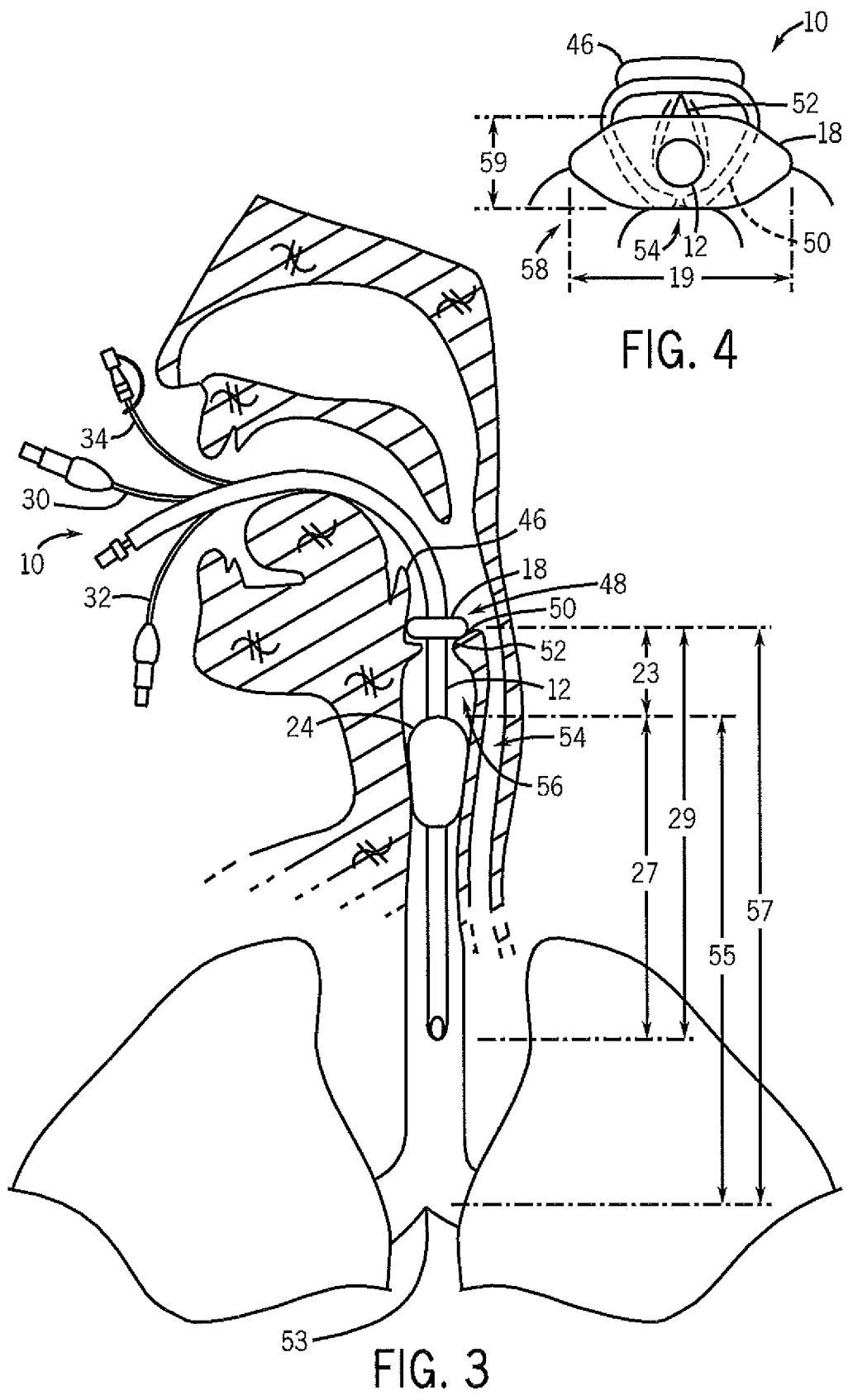

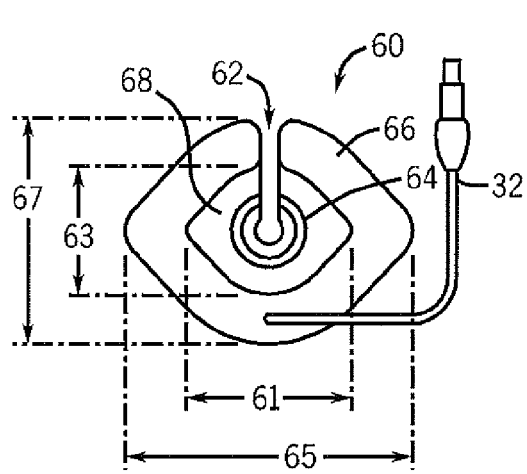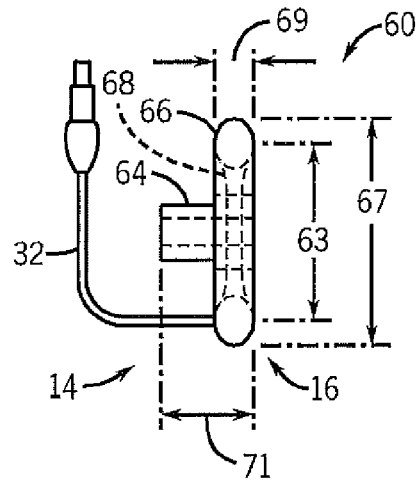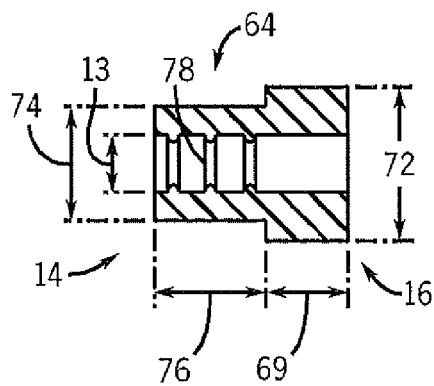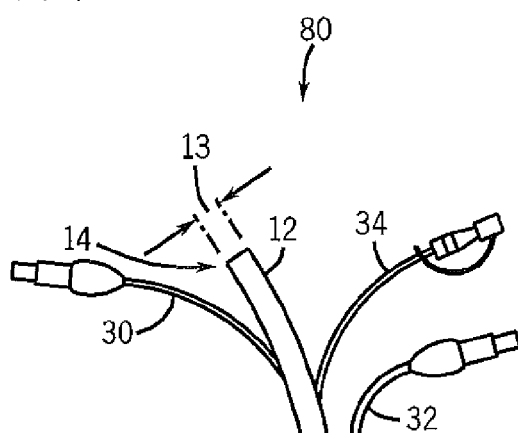

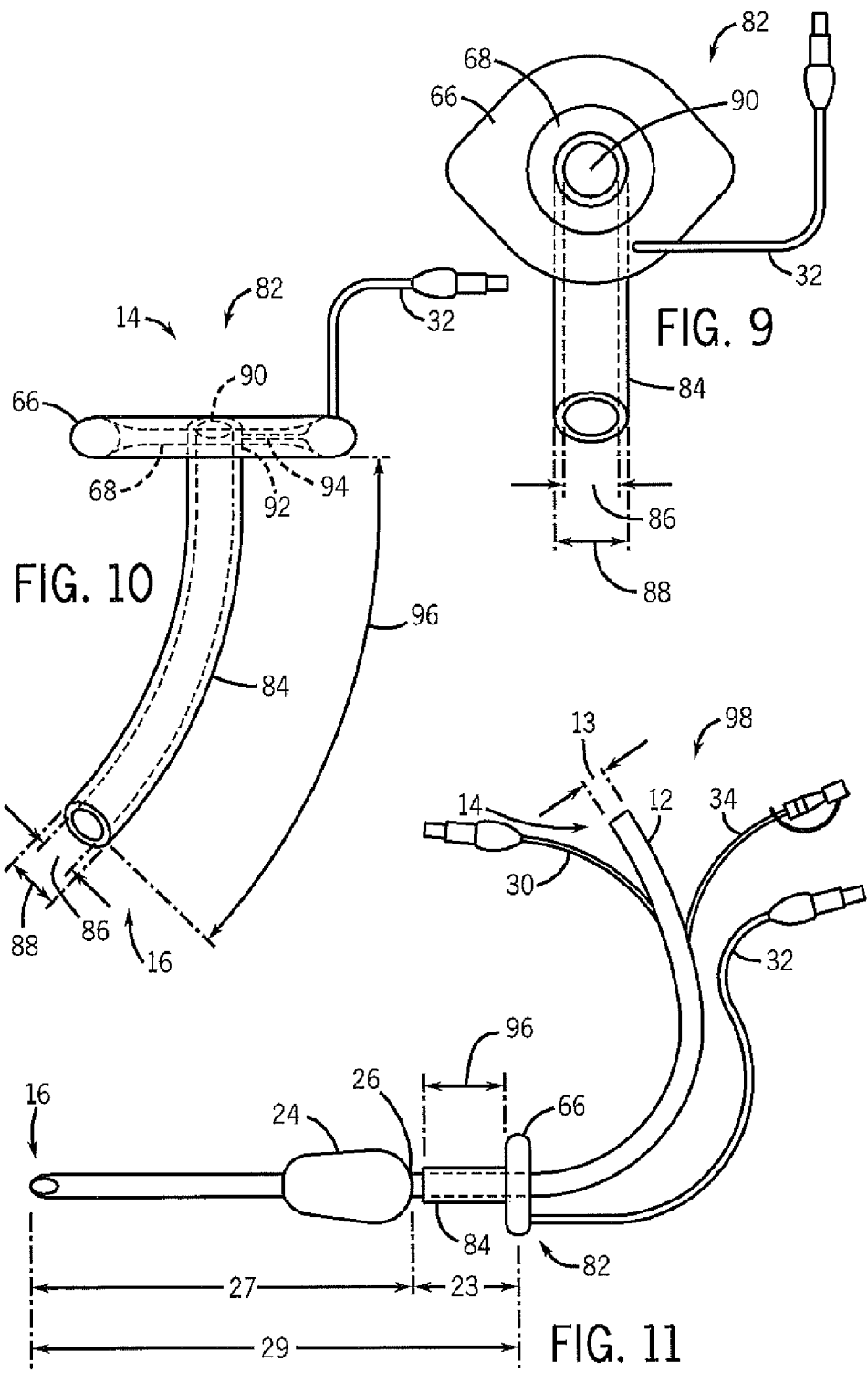

SUPRAGLOTTIC FIXATION DEVICE FOR ENDOTRACHEAL TUBES

BACKGROUND

The present disclosure relates generally to medical devices and, more particularly, to airway devices, such as endotracheal tubes (ETTs).

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, medical devices, such as tracheal tubes may be used to control the flow of air or other gases through a trachea of a patient. Such tracheal tubes may include ETTs, tracheotomy tubes, or transtracheal tubes. In many instances, it is desirable to provide a seal between the outside of the tube or device and the interior of the passage in which the tube or device is inserted, typically the trachea in the case of ETTs. In this way, substances can only flow through the passage via the tube or other medical device, allowing a medical practitioner to maintain control over the type and amount of substances flowing into and out of the patient. In addition, a high-quality seal against the tracheal passageway allows a ventilator to perform efficiently.

For example, a patient may be intubated by insertion of an ETT through the mouth and into the trachea. To help ensure maintenance of a proper seal, a health care provider may use a variety of methods to fix the tube in place. For example, many clinicians fix tubes in place using standard medical tape. Even this common method has drawbacks including the possibility of ulceration of the lips and mouth of the patient and eventual loss of adhesion causing subsequent movement of the tube. Unintended movement of the tube further into the patient may cause improper intubation and limited ventilation. Likewise, movement out of the trachea may lead to spontaneous extubation.

BRIEF DESCRIPTION OF THE DRAWINGS

Advantages of the disclosed techniques may become apparent upon reading the following detailed description and upon reference to the drawings in which:

FIG. 3 is a partial cross-sectional view along an airway flow axis of an exemplary ETT disposed in a patient;

FIG. 4 is an inferior view along an airway flow axis of an exemplary ETT disposed in a hypopharynx of a patient.

FIG. 5 is a front perspective view of an exemplary separate inflatable anchoring device for an ETT;

FIG. 6 is a perspective view of an exemplary separate inflatable anchoring device for an ETT;

FIG. 7 is a cross-sectional view of an exemplary compression lock of a separate inflatable anchoring device for an ETT;

FIG. 8 is a perspective view of an exemplary ETT with an installed separate inflatable anchoring device;

FIG. 9 is a front perspective view of an exemplary separate inflatable anchoring device with guidance tube for an ETT;

FIG. 10 is a perspective view of an exemplary separate inflatable anchoring device with guidance tube for an ETT; and FIG. 11 is a perspective view of an exemplary ETT with an installed separate inflatable anchoring device with guidance tube.

DETAILED DESCRIPTION OF SPECIFIC EMBODIMENTS

Figure 1:
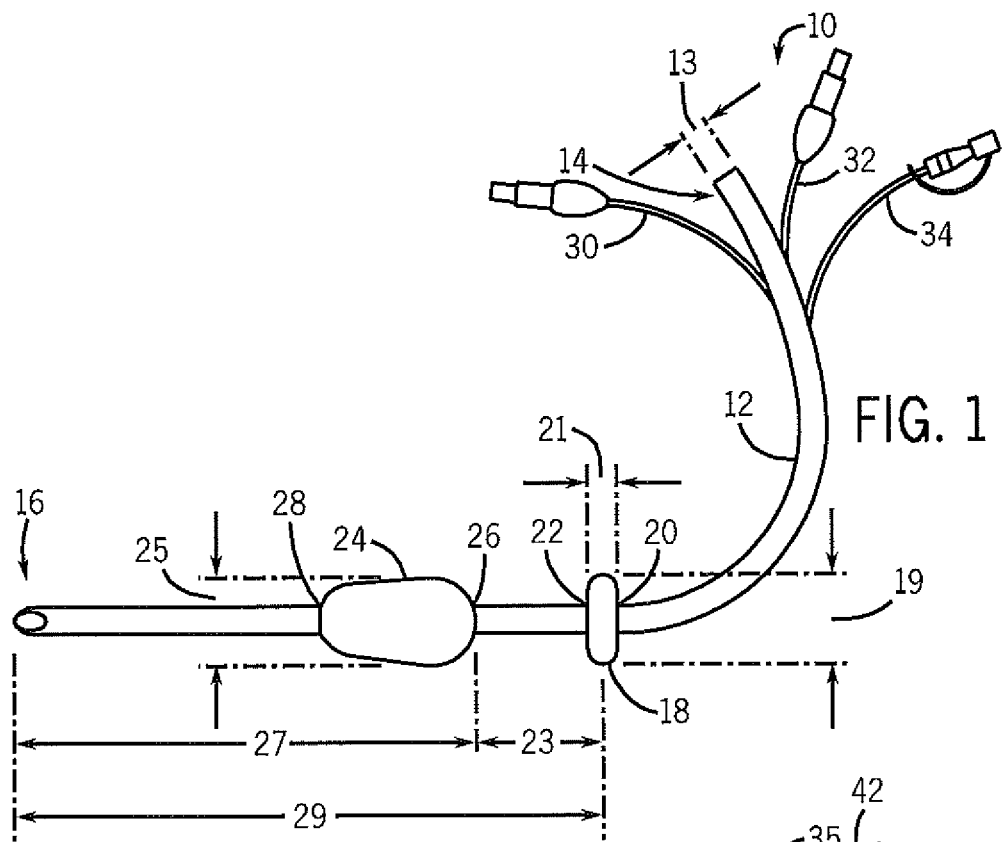
FIG. 1 is a perspective view of an exemplary ETT with an integral inflatable anchoring device.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A tracheal tube ventilating device may be used to seal an airway of a patient and provide positive pressure to the lungs when properly inserted into the trachea. The ventilating gas passing through the tube typically comprises air, but may also include anesthetic gases, medications, or various gas mixtures, such as mixtures containing higher concentrations of oxygen than atmospheric air. In addition, the source of the ventilating gas is typically a medical device such as a ventilator. Positioning the tracheal tube at a desired position within the trachea, for example during endotracheal intubation, may improve the performance of the tracheal tube and reduce clinical complications. In particular, the distal inserted end of the ETT may be positioned in the trachea of a patient at a location substantially between the vocal cords and carina. If the tube is not inserted far enough past the vocal cords, for example, the tube may become more easily dislodged. If the tube is inserted too far into the trachea, such as past the carina, then the tube may only function to adequately ventilate one of the lungs, rather than both. Thus, proper placement of the distal tip of the tube may result in improved ventilation to the patient.

Once a healthcare provider has properly placed the tube in a patient, some method of fixing the tube in place is required to help ensure that the patient continues to be properly ventilated and that the tube cannot easily be extubated accidentally. Provided herein are ETTs and separate devices with features positionable internal to the patient that enable the tubes to be fixed in place. In other words, the anchoring devices of the disclosed embodiments work with the anatomy of a patient to help retain the tube fixed in place with or without the use of methods external to the patient. Moreover, such anchoring devices may be easier and simpler to use than external methods, as the device may be integral with the tube. In addition, internal anchoring devices may be more effective and reliable than external methods as they are typically less susceptible to dislodging accidentally once properly deployed inside the patient. Finally, in the disclosed embodiments, once the anchoring device is inflated or expanded, its increased size aids in anchoring it in place. Thus, an inflatable anchoring device may only need to be inflated to a low pressure to increase its size, and not to a higher pressure as may be required to create a seal against an internal anatomical surface of the patient.

In certain embodiments, the anchoring device may be either an integral part of the ETT or a separate device attached to the ETT after intubation. An advantage of an integral anchoring device is simplicity, while an advantage of a separate device is flexibility. For example, in some situations, the patient may initially need to be intubated for only a short period, during which an external method such as using medical tape may be appropriate. However, changed circumstances may require longer intubation. In that case, a separate anchoring device that can be inserted into the patient without disturbing the existing intubation may be desirable. In addition, a separate anchoring device can be removed, if necessary, without affecting the intubation of the patient. Further, in certain embodiments, the separate anchoring device may be provided with a guidance tube or similar structure. Thus, the device would be first placed in the patient and then the guidance tube used to properly insert an ETT. When the anchoring device is separate from the ETT, some method of retaining the device in place on the ETT is necessary. A number of methods may be employed, such as interference fits created by ribs or an inflatable inner cuff.

In all the disclosed embodiments, the primary function of the anchoring device is to securely retain the ETT in place. In other words, the anchoring device is not designed to provide a seal against the trachea wall. Therefore, the design and shape of the anchoring device is such that an airtight seal of the hypopharynx is not possible. Further, the anchoring device is not designed to block the esophagus of a patient. Thus, the anchoring device will not likely interfere with other medical devices, such as feeding tubes, which may need to be placed in the esophagus. Instead, the anchoring device resides superior to the aryepiglottic fold and in contact with the piriform fossa on either side of the glottis. Thus, the device may be described as supraglottic because it resides superior to the glottis. In a presently contemplated embodiment, when properly positioned, the anchoring device is only in contact with the left and right lateral sides of the piriform fossa and a laryngeal surface of the epiglottis.

As with the sealing cuff of an ETT, the anchoring device is designed to be smaller when inserted into or removed from a patient and larger when in position to anchor the ETT in place. A number of methods may be used to accomplish this change in size. For example, the anchoring device may be inflatable or may comprise mechanical means of expanding or collapsing. As with conventional sealing cuffs, a lumen may be provided for inflating or deflating an inflatable anchoring device. In addition, all the disclosed embodiments may be fabricated in different sizes and configurations to accommodate differences in the age or anatomy of the patient population.

In certain embodiments, the disclosed tracheal tubes, systems, and methods may be used in conjunction with any appropriate medical device, including without limitation a feeding tube, an ETT, a tracheotomy tube, a circuit, an airway accessory, a connector, an adapter, a filter, a humidifier, a nebulizer, nasal cannula, or a supraglottic mask/tube. The present techniques may also be used to treat any patient benefiting from mechanical ventilation, e.g., positive pressure ventilation. Further, the devices and techniques provided herein may be used to treat human patients, such as trauma victims, patients with tracheotomies, anesthetized patients, cardiac arrest victims, patients suffering from airway obstructions, and patients suffering from respiratory failure.

FIG. 1 is a perspective view of an embodiment of an ETT 10 with an inflatable anchoring device 18. In the illustrated embodiment, the ETT 10 comprises a tubular body 12 with an outside diameter 13. In certain embodiments, the outside diameter 13 of the tubular body 12 may be between approximately 2 and 13 mm. The tubular body 12 comprises a proximal end 14 and a distal end 16. The inflatable anchoring device 18 is secured to the tubular body 12 near the distal end 16. The anchoring device 18 may be fixed in place on the tubular body 12 or may be attached in such a way as to allow it to move a small amount proximally or distally along the tubular body 12. In certain embodiments, the anchoring device 18 may be able to move approximately between 1 to 3 cm along the tubular body 12. In addition, the anchoring device 18 may comprise a material that is more rigid than that typically used for inflatable sealing cuffs. As the purpose of the inflatable anchoring device 18 is not to create a seal with the tissue of a patient, it is less important that the material be as soft and pliable. Exemplary categories of materials may include thermoplastic elastomers including styrene block copolymers, polyolefin blends, thermoplastic poly(urethane)s, thermoplastic copolyesters, thermoplastic poly(amide)s, or mixtures thereof. Specific examples of materials may include latex, rubber, nitrile, poly(urethane), poly(ethylene), poly (ethylene terephthalate) (PET), poly(vinyl chloride) (PVC), silicone, siloxane, poly(propylene), or mixtures thereof. In addition, the stiffness and/or durometer of the anchoring device 18 may be modulated by material choice, usage of plasticizers and additives, varying thickness, or creating textures on the material surface. Further, creating a texture, which may include using microbarbs, may facilitate enhanced anchoring. Usage of a coating or a bulk mucoadhesive as a component of the anchoring device 18 may also improve fixation. Examples of mucoadhesives may include hydroxypropyl methyl cellulose, carboxymethyl cellulose, poly(ethylene oxide), poly(vinyl alcohol), poly(vinyl pyrrolidone), or mixtures thereof.

When fully inflated, the anchoring device 18 has a widest dimension 19 and a thickness 21. It should be noted that, in presently contemplated embodiments, the device is not radially symmetrical, though it is bilaterally symmetrical. In certain embodiments, the widest dimension 19 may be between approximately 3 and 9 cm and the thickness 21 of the device may be between approximately 1 and 3 cm. The widest dimension 19 and the thickness 21 are configured so that the anchoring device 18 may be positioned completely within the hypopharynx of a patient, in contact with the piriform fossa and a laryngeal surface of the epiglottis without creating an airtight seal of either the hypopharynx or the esophagus. Accordingly, proper sizing and inflation of the anchoring device 18 may reduce the risk of both excessive displacement of the ETT 10 into the trachea and possible accidental extubation. In certain embodiments, the inflation pressure of the device may be between approximately about 5 and 10 cm $H_2O$. In addition, the outer peripheral shape of the anchoring device 18 may be configured to conform to the epiglottis, the piriform fossa, or both. The anchoring device 18 comprises a proximal side 20 and a distal side 22. The distal side is positioned towards the lower respiratory tract, while the proximal side is oppositely oriented. At least portions of the distal side may aid in supporting and positioning the device when properly installed.

A sealing cuff 24 is secured to the tubular body 12 near the distal end 16, below the anchoring device 18, and extends outwardly from the tubular body 12. The sealing cuff 24 may be inflatable. When fully inflated, the sealing cuff 24 has an outside diameter 25 and acts to create a seal between the trachea wall and the ETT 10. In certain embodiments, the outside diameter 25 of the sealing cuff 24 may be between approximately 4 and 15 mm to accommodate different patient sizes. As with the anchoring advice 18, the sealing cuff 24 comprises a proximal side 26 and a distal side 28. The proximal side 26 of the sealing cuff 24 may be positioned a distance 23 from the midline of anchoring device 18, the midline passing orthogonally to an airway flow axis of the ETT 10. In certain embodiments, the distance 23 may be between approximately 8 and 10 cm to help ensure that the anchoring device 18 is properly positioned in the hypopharynx. In addition, the proximal side 26 of the sealing cuff 24 may be positioned a distance 27 from the distal tip of the tubular body 12. Moreover, the distance 27 from the proximal side 26 of the sealing cuff 24 to the distal tip of the tubular body 12 may be between approximately 4 and 6 cm to help ensure that the sealing cuff 24 is properly positioned in the trachea. Further, the midline of anchoring device 18 may be positioned a distance 29 from the distal tip of the tubular body 12. The distance 29 may be between approximately 12 and 16 cm.

Other features shown in FIG. 1 include a small vent that may be provided on the distal tip of the tubular body 12. Such a vent (commonly called a Murphy eye) may reduce the risk of right bronchial occlusion. In addition, an inflation lumen 30 may be used to inflate and deflate the sealing cuff 24 and a separate inflation lumen 32 may be used to inflate and deflate the anchoring device 18. Separate lumens are provided as the pressures of the sealing cuff 24 and the anchoring device 18 will likely not be the same. In certain embodiments, the pressure of the sealing cuff 24 may be between approximately about 20 and 30 cm $H_2O$. For example, the pressure of the sealing cuff 24 may be approximately 100 to 500%, 100 to 250%, or 100 to 150% greater than the pressure of the inflatable anchoring device 18. The ETT 10 may be provided with a suction lumen 34 to remove secretions that may accumulate above the sealing cuff 24. Finally, the tubular body 12, lumens 30, 32, and 34, sealing cuff 24, and other components found in ETTs may comprise materials commonly used for such components.

Figure 2:
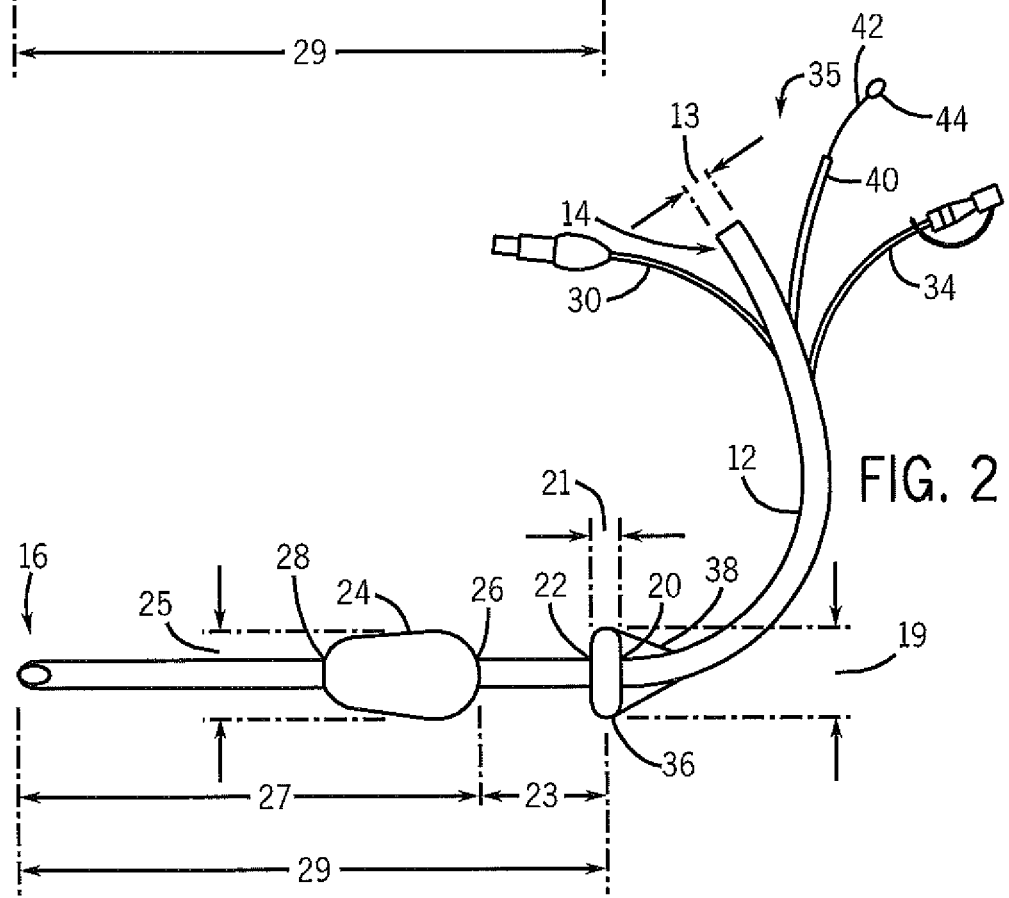
FIG. 2 is a perspective view of an exemplary ETT with an integral mechanical anchoring device.

FIG. 2 is a perspective view of an embodiment of an ETT 35 with a mechanical anchoring device 36. In the illustrated embodiment, the mechanical anchoring device 36 is secured to the tubular body 12 near the distal end 16. An actuating means 38 coupled to the anchoring device 36 acts to either expand or collapse the device in response to movement of an actuating pull 44. The actuating pull 44 is disposed on the end of an actuating member 42, which is partially disposed in an actuating lumen 40 coupled to tubular body 12. Other methods such as, but not limited to resilient foams, electroactive polymers, shape-shifting polymers, or piezoelectric materials, may also be used to comprise the anchoring device. Such methods should be capable of reducing the size of the anchoring device during intubation or extubation and increasing the size once in place to anchor the tube properly. Other elements shown in FIG. 2 in common with those shown in FIG. 1 are discussed above.

FIG. 3 shows an ETT 10 with an inflatable anchoring device 18 disposed in a patient. In the illustrated embodiment, the anchoring device 18 is in contact with an epiglottis 46 and an aryepiglottic fold 50 of the patient, but not the esophagus 54. Thus, the anchoring device 18 resides completely within a hypopharynx 48 of the patient, without creating an airtight seal of the esophagus 54. The tubular body 12 passes through a glottis (vocal cords) 52 and the sealing cuff 24 resides in a trachea 56. Displacement of the ETT 10 far enough into the trachea 56 such that the distal tip contacts a carina 53 is avoided. To reduce the risk of such a possibility, the proximal side 26 of the sealing cuff 24 may be positioned a distance 55 to the carina 53 and the midline of anchoring device 18 may be positioned a distance 57 to the carina 53. In certain embodiments, the distance 55 may be between approximately 4 and 6 cm and the distance 57 may be between approximately 8 and 13 cm. Other elements shown in FIG. 3 in common with those shown in FIG. 1 are discussed above.

FIG. 4 is an inferior view of an embodiment of an ETT 10 with an inflatable anchoring device 18 disposed in the hypopharynx of a patient. In the illustrated embodiment, the glottis 52 is located posterior to the epiglottis 46 and anterior to the esophagus 54. The tubular body 12 of the ETT 10 passes through the glottis 52. The anchoring device 18 resides superior to the aryepiglottic fold 50 and in contact with a piriform fossa 58 on either side of the glottis 52. In the particular embodiment shown, the widest dimension 19 is such that the device is in contact with both the left and right lateral sides of the piriform fossa 58. Further, a minimum width 59 of the anchoring device 18 is such that the device does not completely cover the opening of the glottis 52. In certain embodiments, the minimum width 59 may be between approximately 2 and 7 cm. This helps to ensure that the anchoring device 18 does not create an airtight seal of the hypopharynx, but instead acts to anchor the ETT 10 in place.

FIG. 5 is a front view of an embodiment of a separate inflatable anchoring device 60 capable of being secured to an ETT. In the illustrated embodiment, an opening 62 enables the anchoring device 60 to be placed on an ETT and slid distally down the ETT with a tool such as a stylet without the need to remove the ETT from the patient or disconnect any fittings located at the proximal end of the ETT. A similar device could be snapped to the ETT prior to intubation. Thus, the anchoring device may be secured to the ETT after the patient has been intubated with the ETT. A compression lock 64 is located at the center of the anchoring device 60 and secures the device to the ETT. In addition, once the anchoring device 60 is properly secured to the ETT by the compression lock 64, the device reduces the risk of the ETT being accidentally extubated or excessively displaced into the trachea. Further details of the compression lock are discussed below and shown in FIG. 7.

The anchoring device 60 further comprises an inner non-inflatable region 68 that surrounds the compression lock 64. Surrounding the inner non-inflatable region 68 is an outer inflatable region 66, which may be filled or emptied using an inflation lumen 32. Alternatively, in certain embodiments, the outer inflatable region 66 may comprise a soft, conformable, and resilient non-inflatable material, such as, but not limited to, polyurethane. Examples of materials that may be used in the outer inflatable region 66 include, but are not limited to, PVC. The inner non-inflatable region 68 may comprise a harder material that helps to provide support for the outer inflatable region 66. Examples of materials that may be used in the inner non-inflatable region 68 include, but are not limited to, polytetrafluoro ethylene (PTFE).

In the particular embodiment shown, the anchoring device 60 is bilaterally symmetrical but not radially symmetrical. Therefore, the width in one direction is less than the width in an orthogonal direction. Thus, the inner non-inflatable region 68 has a maximum width 61 that is greater than a minimum width 63. In certain embodiments, the maximum width 61 of the inner non-inflatable region 68 may be between approximately 2 and 8 cm and the minimum width 63 may be between approximately 1 and 6 cm. Further, the outer inflatable region 66 has a maximum width 65 that is greater than a minimum width 67. In certain embodiments, the maximum width 65 of the outer non-inflatable region 66 may be between approximately 3 and 9 cm and the minimum width 67 may be between approximately 2 and 7 cm. As with the anchoring device 10 shown in FIG. 1, once the anchoring device 60 is secured to the ETT, it is configured so that it may be positioned completely within the hypopharynx of a patient, in contact with the piriform fossa and a laryngeal surface of the epiglottis without creating an airtight seal of either the hypopharynx or the esophagus. Thus, the peripheral shape of the outer inflatable region 66 may be configured to conform to the epiglottis, the piriform fossa, or both. As with the anchoring devices integral to an ETT discussed above, the anchoring device 60 is not limited to only the embodiments disclosed, but may comprise any other method such as resilient foams, electroactive polymers, shape-shifting polymers, or piezoelectric materials. Finally, lumen 32, compression lock 64, and other components found in ETTs may comprise materials commonly used for such components.

FIG. 6 is a side view of the inflatable anchoring device 60 shown in FIG. 5. In the illustrated embodiment, the anchoring device 60 comprises a thickness 69. In certain embodiments, the thickness 69 may be between approximately 1 and 3 cm. The thickness of the inner non-inflatable region 68 may be less than that of the device as it primarily acts only to provide support for outer inflatable region 66. A thickness 71 of the compression lock 64 may be greater than that of the anchoring device 60 as it helps to retain the device in place on the ETT after placement. In certain embodiments, the thickness 71 of the compression lock 64 may be between approximately 3 and 5 cm. The anchoring device 60 further comprises a proximal side 14 and a distal side 16. The inflation lumen 32 extends from the proximal side 14 of the device and out through the mouth of the patient. Other elements shown in FIG. 6 in common with the anchoring device 60 shown in FIG. 5 are discussed above.

FIG. 7 is a cross-sectional view of the compression lock 64 shown in FIG. 5. In the illustrated embodiment, an outside diameter 72 of the portion of the compression lock 64 disposed internal to the anchoring device 60 may be greater than an outside diameter 74 of the portion of the compression lock 64 disposed external to the device. A greater internal diameter may enable the compression lock 64 to be better integrated into the structure of the inner non-inflatable region 68. In certain embodiments, the diameter 72 internal to the anchoring device 60 may be between approximately 2.5 and 13.5 cm and the outside diameter 74 disposed external to the device may be between approximately 2.25 and 13.25 cm. In other embodiments, the two diameters 72 and 74 may be the same. Further, the portion of the compression lock 64 external to the anchoring device 60 comprises a length 76. A sufficiently long compression lock 64 will provide enough surface area in contact between the lock 64 and the ETT to help retain the ETT in place. In certain embodiments, the external length 76 of the compression lock 64 may be between approximately 2 and 3 cm. The inner surface of compression lock 64 comprises a plurality of ribs 78 that protrude inward creating areas where the inner diameter of the compression lock 64 is slightly less than the outside diameter 13 of the ETT. Thus, a series of interference fits is created that helps retain the ETT in place. Other methods of restraining the anchoring device 60 in place on the ETT may be utilized, such as an inner inflatable cuff similar to that discussed below with respect to FIG. 10. In such a cuff, inflation lumen 32 may be used to simultaneously inflate both outer inflatable region 66 and the inner inflatable cuff to secure the anchoring device 60 to the ETT.

FIG. 8 is a perspective view of an embodiment of an ETT 80 subsequent to having a separate inflatable anchoring device 60 secured to it. As with the anchoring device 10 shown in FIG. 1, after the device has been secured in place by a compression lock 64, the midline of the device may be located a distance 23 from the proximal side 26 of the sealing cuff 24. In addition, the midline of anchoring device 60 may be positioned a distance 29 from the distal tip of the tubular body 12. To extubate the patient, both the anchoring device 60 and the sealing cuff 24 are deflated and may be removed together without need to remove the device separately. Other elements shown in FIG. 8 in common with those shown in FIG. 1 are discussed above.

FIG. 9 is a front view of an embodiment of a separate inflatable anchoring device 82 with a guidance tube 84. In the illustrated embodiment, the anchoring device 82 is similar to the anchoring device 60 shown in FIG. 5. Additionally, the guidance tube 84 is secured to the distal side 16 of the device to help guide an ETT into place in the trachea of the patient. The guidance tube 84 comprises an inner diameter 86 and an outer diameter 88. In certain embodiments, the inner diameter 86 may be between approximately 2 and 13 cm and the outer diameter 88 may be between approximately 2.25 and 13.25 cm. The guidance tube 84 comprises a flexible material to help it conform to the particular anatomy of a patient. In certain embodiments, the guidance tube 84 may comprise a material that is both flexible and yet somewhat rigid. Examples of materials that may be used in the guidance tube 84 include, but are not limited to, PVC, poly(phenyl ether)s, PTFE, latex, rubber, nitrile, PET, silicone, or mixtures thereof. A proximal opening 90 of the guidance tube 84 is located in the center of the anchoring device 82. As with the anchoring devices integral to an ETT discussed above, the anchoring device 82 is not limited to only the embodiments disclosed, but may rely on any other method and structure to define its shape, to secure it to the ETT, and to retain it in the desired location, such as resilient foams, electroactive polymers, shape-shifting polymers, or piezoelectric materials. Other elements shown in FIG. 9 in common with those shown in FIG. 5 are discussed above.

FIG. 10 is a side view of the separate inflatable anchoring device 82 shown in FIG. 9. In the illustrated embodiment, the anchoring device 82 further comprises an inflatable inner cuff 92 that secures the device to an ETT. A lumen 94 connects the inner cuff 92 with the outer inflatable region 66. Thus, when inflation lumen 32 is used to inflate the outer inflatable region 66, the inner cuff 92 also inflates exerting inward pressure on the ETT. In other words, the inner diameter of the inflated inner cuff 92 is slightly less than the outside diameter 13 of the ETT. Thus, an interference fits is created that helps retain the ETT in place after intubation, which may reduce the risk of accidental extubation or excessive displacement into the trachea. The guidance tube 84 comprises a length 96, In certain embodiments, the length 96 may be between approximately 7 and 9 cm. In the particular embodiment shown, the inner non-inflatable region 68 slopes down from the outer inflatable region 66 to the opening 90 of the guidance tube 84, which helps to guide the ETT into the opening. The anchoring device 82 may be placed in proper position in the patient using an appropriate tool, such as a stylet. The inflation lumen 32 extends from the proximal side 14 of the device, out through the mouth of the patient, and may comprise materials commonly used for ETT lumens.

FIG. 11 is a perspective view of an embodiment of an ETT 98 subsequent to having a separate inflatable anchoring device 82 with a guidance tube 84 secured to it. As with the anchoring device 10 shown in FIG. 1, after the anchoring device 82 has been secured in place by an inflatable inner cuff 92 (not shown), the midline of the device may be located a distance 23 from the proximal side 26 of the sealing cuff 24. In addition, the midline of anchoring device 82 may be positioned a distance 29 from the distal tip of the tubular body 12. The length 96 of the guidance tube 84 may be less than the distance 23 between the anchoring device 82 and a sealing cuff 24 so that the guidance tube does not interfere with the sealing cuff 24. To extubate the patient, both the device and the sealing cuff 24 are deflated and may be removed together without need to remove the device separately. Other elements shown in FIG. 11 in common with those shown in FIG. 1 are discussed above.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. An endotracheal tube ventilating device comprising:
a tubular body configured to be inserted into the trachea of a patient;
a sealing cuff secured to the tubular body near a distal end of the tubular body; and
an anchoring device secured to the tubular body above the sealing cuff and extending outwardly from the tubular body, the anchoring device being configured to be positioned completely within the hypopharynx of the patient, in contact with the piriform fossa and a laryngeal surface of the epiglottis without creating an airtight seal of the hypopharynx or the esophagus, wherein the anchoring device comprises an inner non-inflatable region surrounded by an outer inflatable region.

2. The endotracheal tube ventilating device of claim 1, wherein the outer inflatable region comprises an inflatable cuff.

3. The endotracheal tube ventilating device of claim 2, wherein the inflatable cuff of the outer inflatable region is made of a material selected from the group consisting of styrene block copolymers, polyolefin blends, thermoplastic poly(urethane)s, thermoplastic copolyesters, thermoplastic poly(amide)s, latex, rubber, nitrile, poly(urethane), poly(ethylene), poly(ethylene terephthalate), poly(vinyl chloride), silicone, siloxane, poly(propylene), plasticizers, additives, microbarbs, hydroxypropyl methyl cellulose, carboxymethyl cellulose, poly(ethylene oxide), poly(vinyl alcohol), poly(vinyl pyrrolidone), or mixtures thereof.

4. The endotracheal tube ventilating device of claim 2, wherein the anchoring device is configured to move either distally or proximally along the endotracheal tube a distance of less than three centimeters.

5. The endotracheal tube ventilating device of claim 1, wherein the outer inflatable region comprises an electroactive polymer adapted to expand upon application of an electrical potential.

6. The endotracheal tube ventilating device of claim 1, wherein the tubular body is operatively connected to a ventilator.

7. The endotracheal tube ventilating device of claim 1, wherein the anchoring device is removably secured to the tubular body.

8. The endotracheal tube ventilating device of claim 7, wherein the anchoring device is secured to the tubular body with a compression lock comprising a plurality of internal ribs that exert force against the tubular body to resist movement.

9. The endotracheal tube ventilating device of claim 7, wherein the anchoring device is secured to the tubular body by an inner inflatable cuff that exerts force against the tubular body to resist movement.

10. The endotracheal tube ventilating device of claim 9, wherein the anchoring device further comprises a flexible distal guidance tube that extends into the trachea of the patient.

11. The endotracheal tube ventilating device of claim 1, wherein the anchoring device is positioned along the tubular body at a location determined by a desired depth of insertion of the tubular body into the trachea of the patient.

12. The endotracheal tube ventilating device of claim 1, wherein the anchoring device is positioned along the tubular body at a location determined by a desired position of a distal tip of the tubular body with respect to the carina of the patient.

13. The endotracheal tube ventilating device of claim 1, wherein the anchoring device is bilaterally symmetrical about a flow axis of the tubular body but not radially symmetrical about the flow axis of the tubular body.

14. The endotracheal tube ventilating device of claim 1, wherein the outer inflatable region has an outer peripheral shape configured to conform to the epiglottis.

15. The endotracheal tube ventilating device of claim 1, wherein the outer inflatable region has an outer peripheral shape configured to conform to the piriform fossa.

16. The endotracheal tube ventilating device of claim 1, wherein the inner non-inflatable region comprises polytetrafluoroethylene.

17. An endotracheal tube ventilating device comprising:
an anchoring device configured to be removably secured to and extend outwardly from an endotracheal tube;
wherein the anchoring device is configured to be positioned completely within the supraglottic region of the patient, without creating an airtight seal of the hypopharynx or the esophagus; and
wherein the anchoring device comprises an inflatable cuff.

18. The endotracheal tube ventilating device of claim 17, wherein the anchoring device is secured to the endotracheal tube with a compression lock comprising a plurality of internal ribs that exert force against the endotracheal tube to resist movement.

19. The endotracheal tube ventilating device of claim 17, wherein the anchoring device is secured to the endotracheal tube by an inner inflatable cuff that exerts force against the endotracheal tube to resist movement.

20. The endotracheal tube ventilating device of claim 17, wherein the anchoring device further comprises a flexible distal guidance tube that extends into the trachea of the patient.

21. An endotracheal tube ventilating device comprising:
a tubular body configured to be inserted into the trachea of a patient;
a sealing cuff secured to the tubular body near a distal end of the tubular body;
an anchoring device secured to the tubular body above the sealing cuff and extending outwardly from the tubular body, the anchoring device being configured to be positioned completely within the hypopharynx of the patient, in contact with the piriform fossa and a laryngeal surface of the epiglottis without creating an airtight seal of the hypopharynx or the esophagus;
wherein an outer inflatable region of the anchoring device comprises an inflatable cuff;

wherein the tubular body is operatively connected to a ventilator;

wherein the anchoring device is removably secured to the tubular body;

wherein the anchoring device is secured to the tubular body with a compression lock comprising a plurality of internal ribs that exert force against the tubular body to resist movement;

wherein the anchoring device is bilaterally symmetrical about a flow axis of the tubular body but not radially symmetrical about the flow axis of the tubular body; and wherein a widest dimension of the anchoring device is greater than a length dimension along the flow axis of the anchoring device.

* * * * *